US012704507B2

(12) United States Patent
Kim et al.

(10) Patent No.: US 12,704,507 B2
(45) Date of Patent: Aug. 11, 2026

(54) MULTIFUNCTIONAL MAGNETIC-OPTICAL NANOPARTICLES

(71) Applicant: KOREA UNIVERSITY RESEARCH AND BUSINESS FOUNDATION, Seoul (KR)

(72) Inventors: Young Keun Kim, Seoul (KR); Hong En Fu, Seoul (KR); Thomas Myeongseok Koo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 925 days.

(21) Appl. No.: 17/940,254

(22) Filed: Sep. 8, 2022

(65) Prior Publication Data

US 2023/0079702 A1 Mar. 16, 2023

(30) Foreign Application Priority Data

Sep. 14, 2021 (KR) ........................ 10-2021-0122705
Dec. 28, 2021 (KR) ........................ 10-2021-0190186

(51) Int. Cl.

| | |
|---|---|
| ***C09K 11/02*** | (2006.01) |
| ***C09K 11/56*** | (2006.01) |
| ***C09K 11/88*** | (2006.01) |
| ***G01N 21/64*** | (2006.01) |
| ***G01N 33/543*** | (2006.01) |

(52) U.S. Cl.

CPC ........ *G01N 33/54346* (2013.01); *C09K 11/02* (2013.01); *C09K 11/565* (2013.01); *C09K 11/883* (2013.01); *G01N 21/6428* (2013.01); *G01N 33/54326* (2013.01); *G01N 2021/6439* (2013.01)

(58) Field of Classification Search

CPC ..... C09K 11/02; C09K 11/565; C09K 11/883; G01N 33/54326; G01N 33/54346; G01N 21/6428; G01N 2021/6439

USPC ........................................................ 423/592.1

See application file for complete search history.

(56) References Cited

U.S. PATENT DOCUMENTS

| | | | | |
|---|---|---|---|---|
| 7,910,164 B2 * | 3/2011 | Kim ....................... | B82Y 25/00 427/443.1 |
| 8,784,698 B2 * | 7/2014 | Schreuder ............ | C09K 11/025 252/519.51 |

(Continued)

OTHER PUBLICATIONS

Chen, Ou, et al. "Magneto-fluorescent core-shell supernanoparticles." Nature communications 5.1 (2014): 5093, (38 pages).

(Continued)

*Primary Examiner* — Cam N. Nguyen
(74) *Attorney, Agent, or Firm* — NSIP Law

(57) ABSTRACT

The method of preparing multifunctional magnetic-optical nanoparticles, includes: preparing magnetic nanoparticle clusters by mixing an oily phase containing magnetic nanoparticles and an aqueous phase containing a cationic surfactant; coating the magnetic nanoparticle clusters with a water-soluble polymer; and preparing multifunctional magnetic-optical nanoparticles by mixing a cluster solution containing magnetic nanoparticle clusters coated with the water-soluble polymer and a quantum dot solution containing quantum dot nanoparticles, wherein the solvent of the cluster solution has a higher polarity index than the solvent of the quantum dot solution.

19 Claims, 9 Drawing Sheets

Strategy to synthesize multifunctional magnetic-optical nanoparticles

Iron oxide cluster | Multifunctional magnetic-optical nanoparticles | PAA-coated multifunctional magnetic-optical nanoparticle CdSe-CdS QDs Physical adsorption Na-PAA functionalization

(56) References Cited

U.S. PATENT DOCUMENTS

| | | | | |
|---|---|---|---|---|
| 10,689,510 | B2 * | 6/2020 | Kim | C08L 33/12 |
| 10,836,960 | B2 * | 11/2020 | Palazzotto | C09K 11/703 |
| 11,542,430 | B2 * | 1/2023 | Fang | C09K 11/883 |
| 11,779,896 | B2 * | 10/2023 | Kim | B01J 13/02 |
| | | | | 428/402 |
| 2009/0108235 | A1 * | 4/2009 | Ando | C09K 11/883 |
| | | | | 427/213.3 |
| 2013/0037762 | A1 * | 2/2013 | Schrier | H10H 20/823 |
| | | | | 252/519.4 |

OTHER PUBLICATIONS

Kyeong, San, et al. "Fabrication of mono-dispersed silica-coated quantum dot-assembled magnetic nanoparticles." RSC Advances 5.41 (2015): 32072-32077.

Korean Office Action issued on Aug. 14, 2023, in counterpart Korean Patent Application No. 10-2021-0190186 (4 pages in Korean).

* cited by examiner

[Fig. 1A]
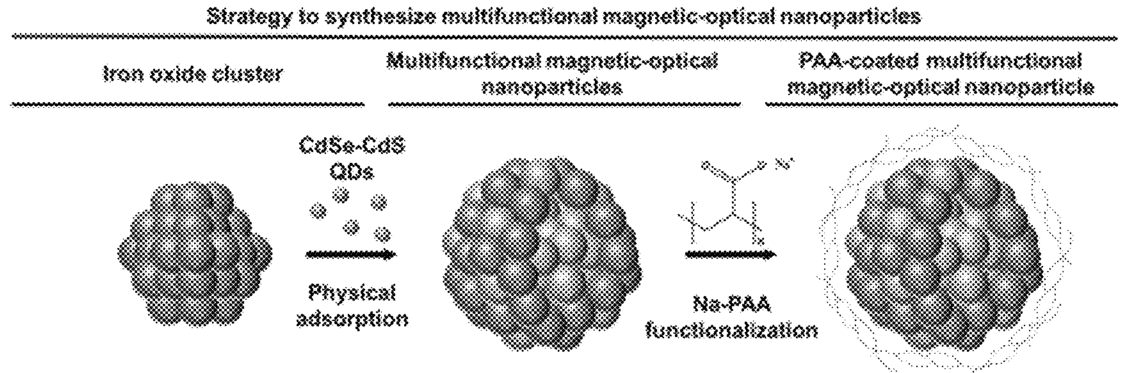
[Fig. 1B]
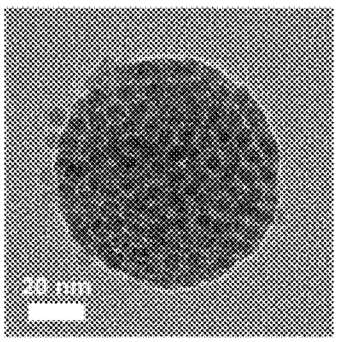
[Fig. 1C]
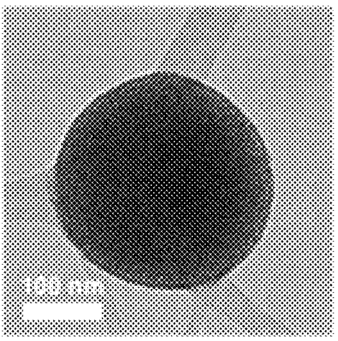

[Fig. 1D]
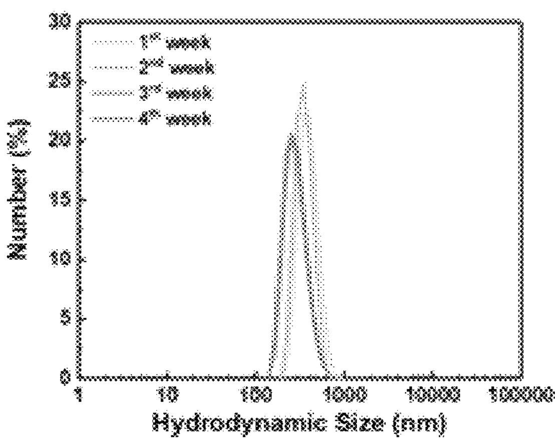
[Fig. 2A]
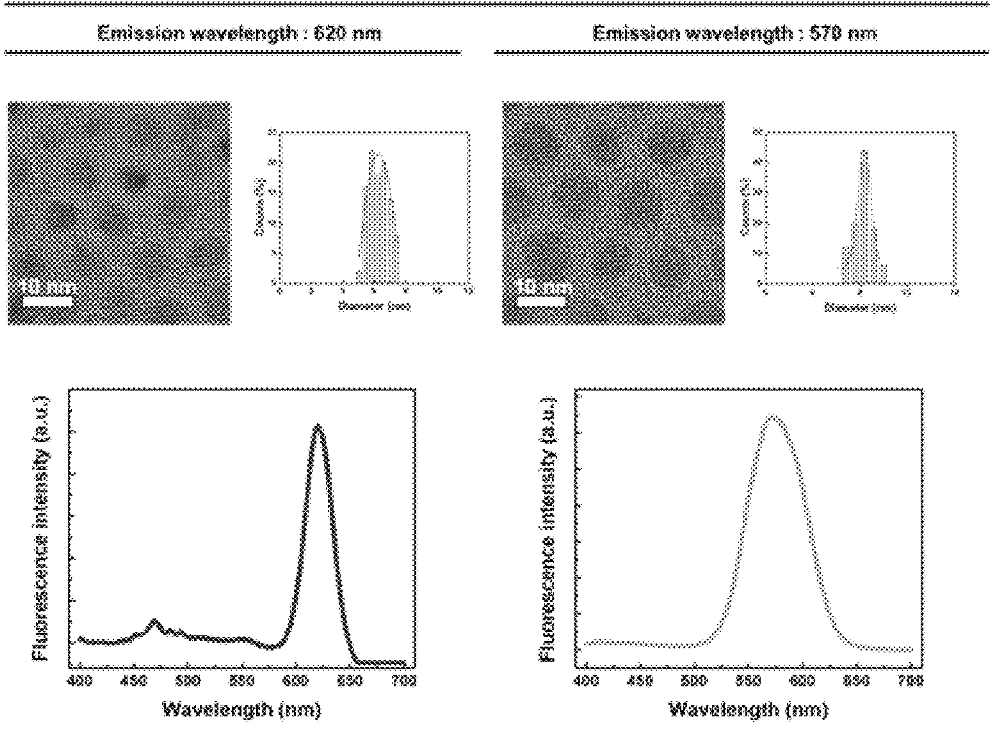

[Fig. 2B]
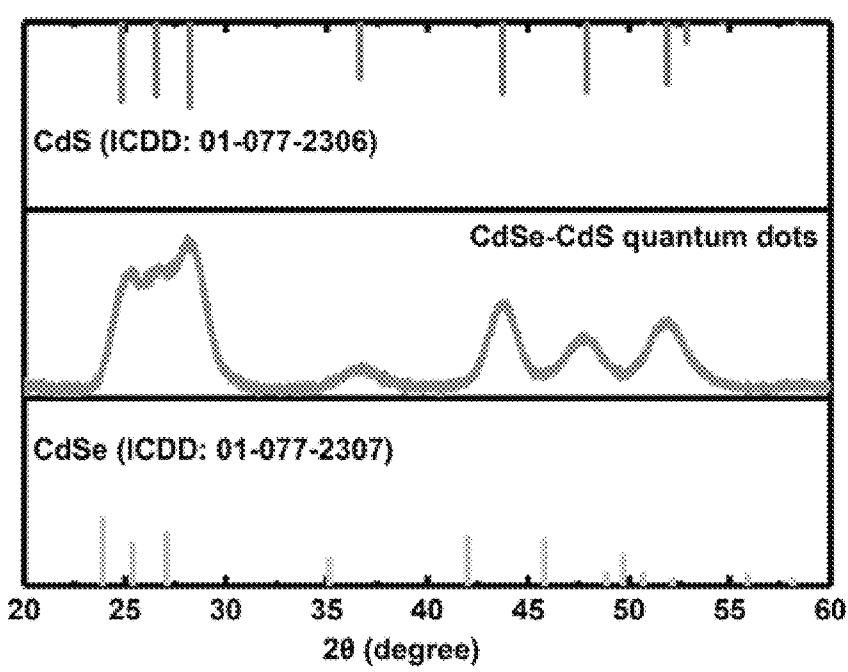

[Fig. 3A]
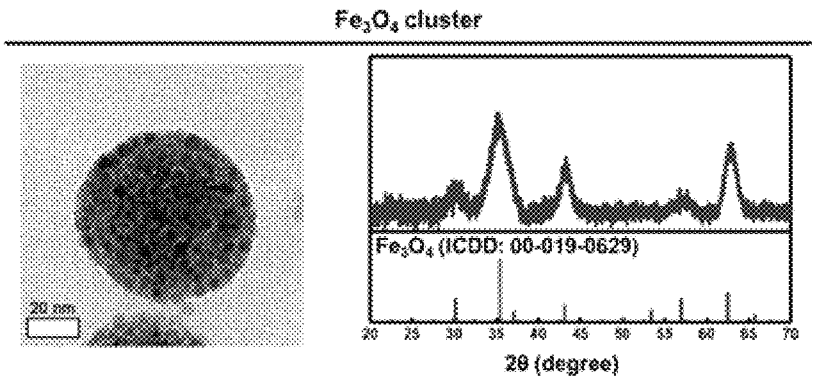
[Fig. 3B]
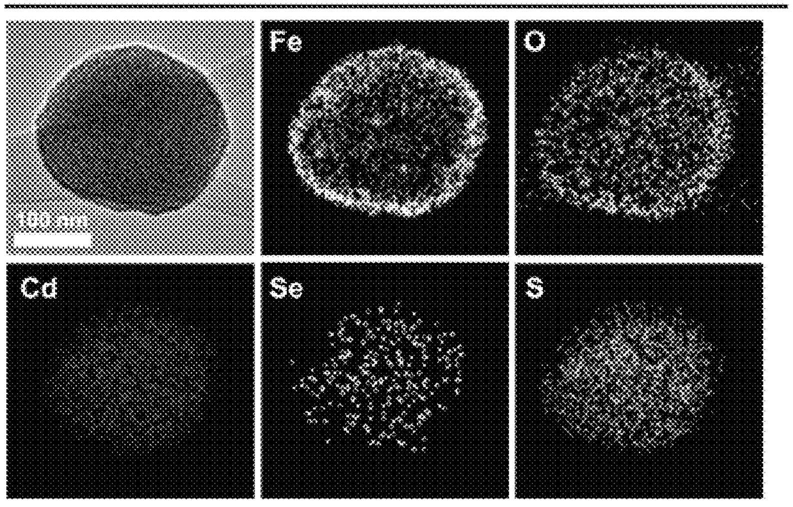

[Fig. 3C]
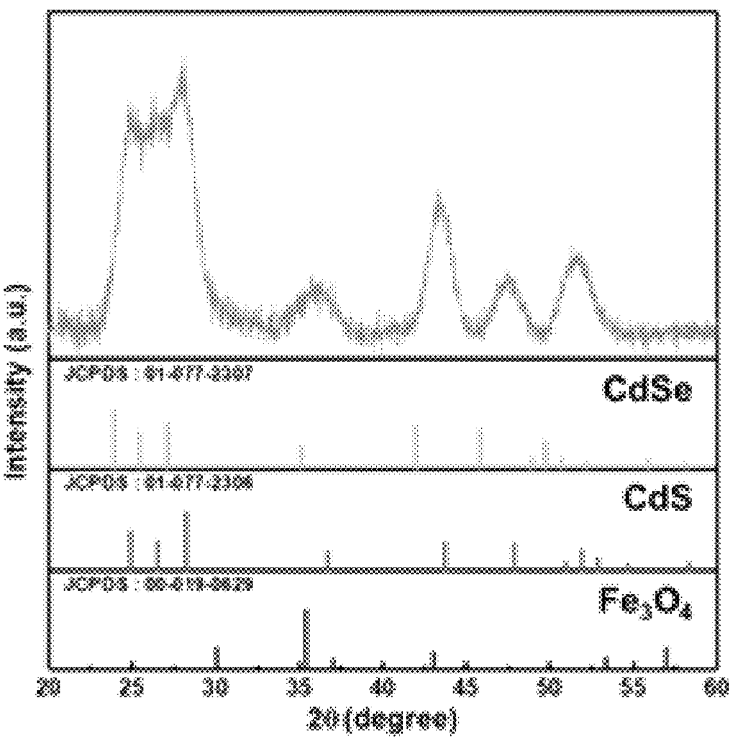
[Fig. 3D]
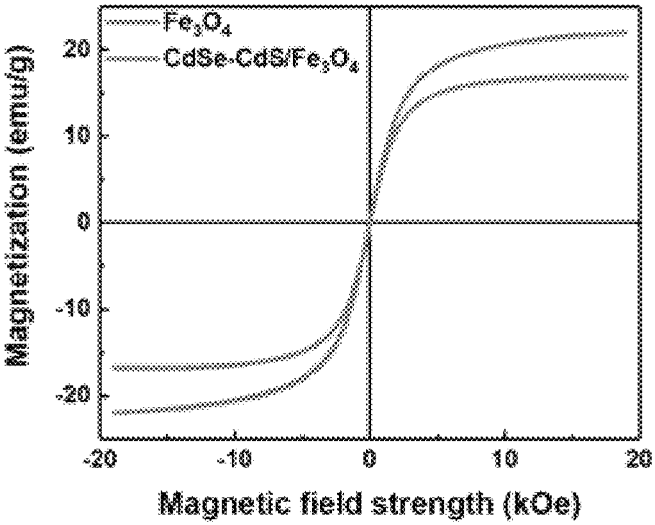

[Fig. 4A]
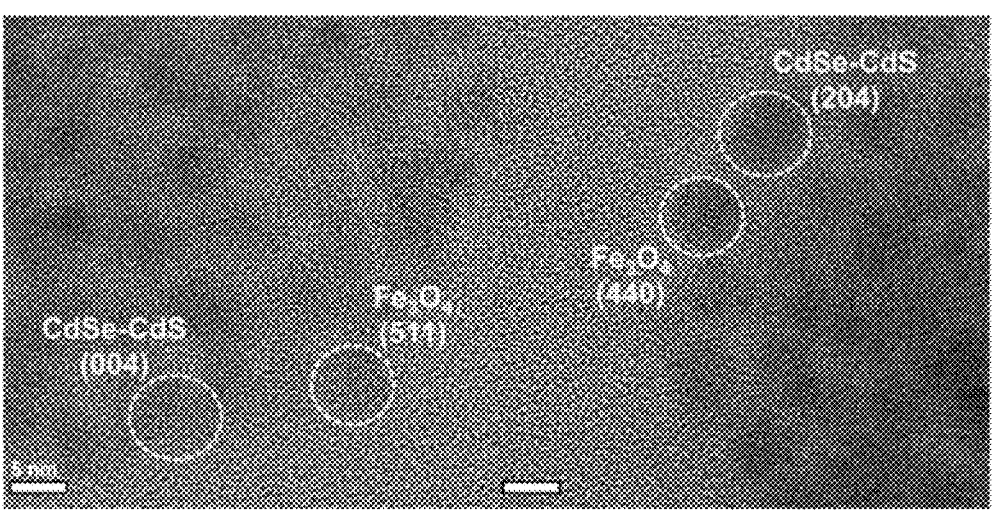
[Fig. 4B]
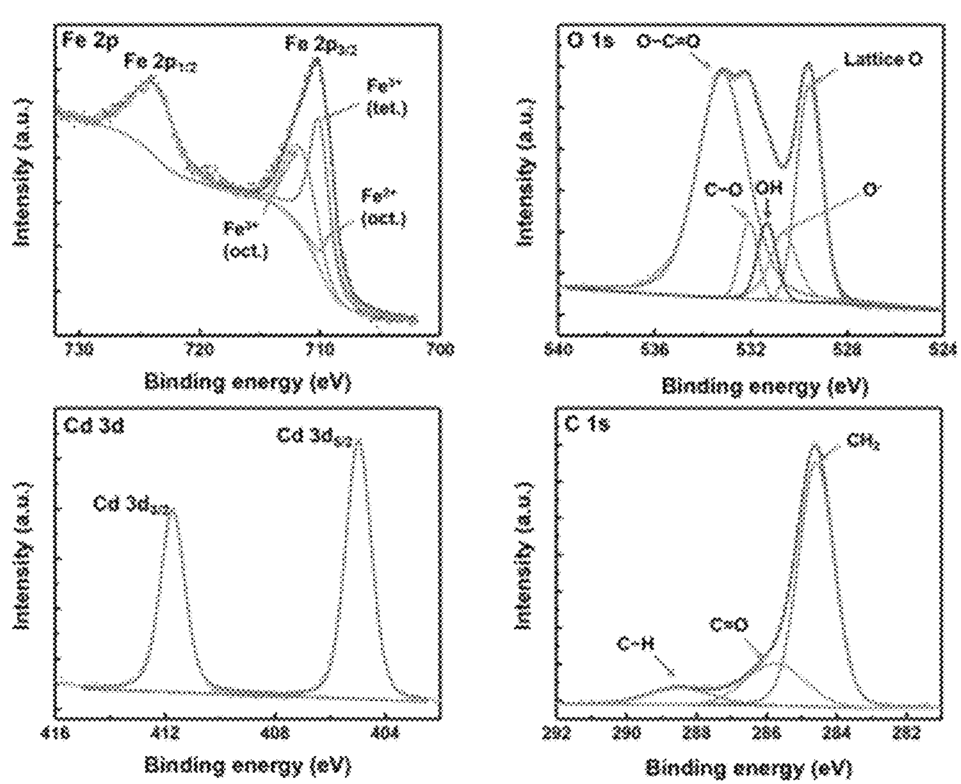

[Fig. 5A]
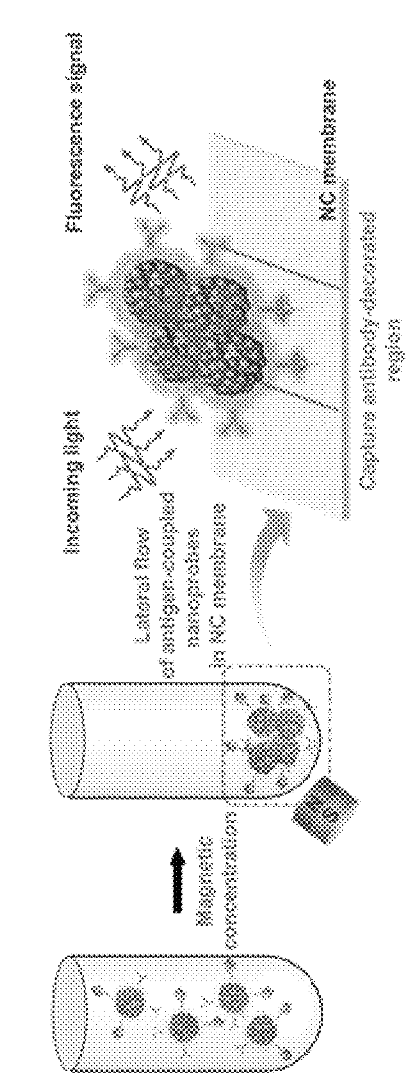

[Fig. 5B]
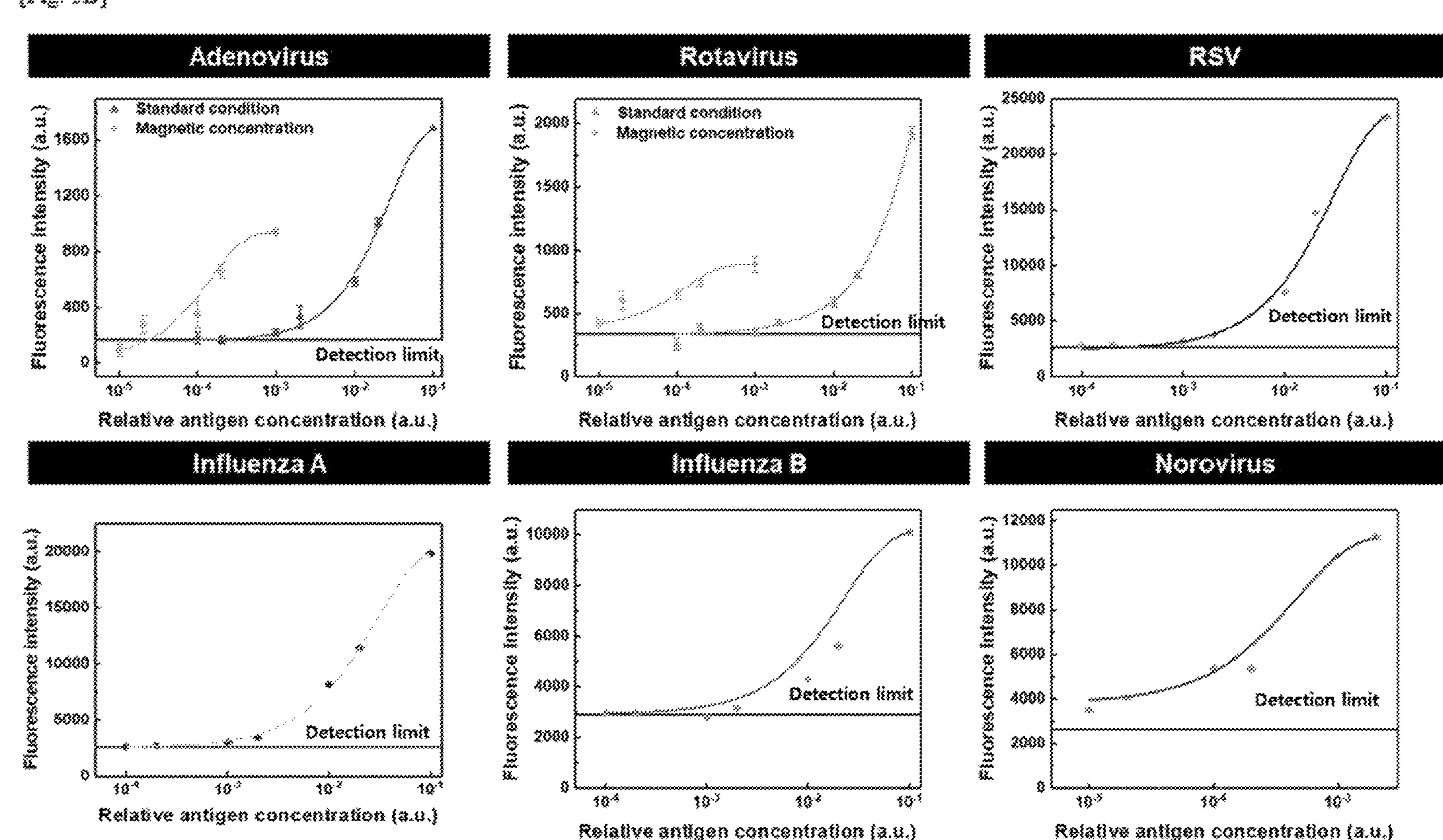

[Fig. 5C]
Confocal imaging of U87MG cells decorated with multifunctional magnetic-optical nanoparticles
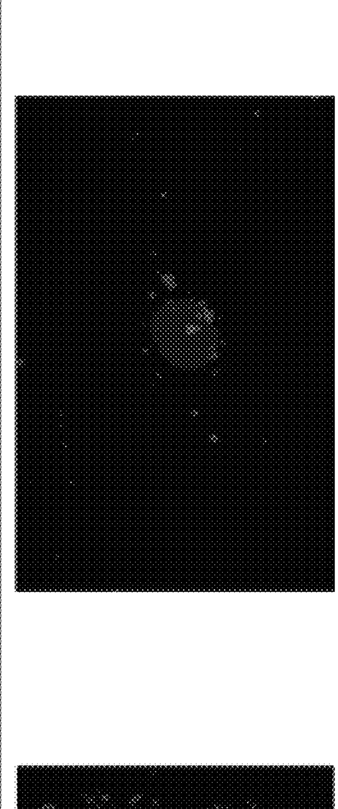
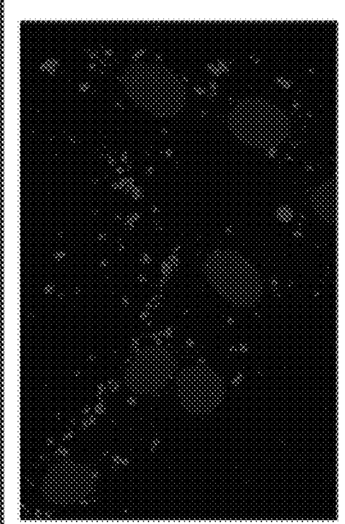

MULTIFUNCTIONAL MAGNETIC-OPTICAL NANOPARTICLES

CROSS-REFERENCE TO RELATED APPLICATION

This application claims priority to Korean Patent Application Nos. 10-2021-0122705, filed on Sep. 14, 2021 and 10-2021-0190186, filed on Dec. 28, 2021, in the Korean Intellectual Property Office, the disclosures of which are incorporated herein by reference.

1. FIELD OF THE INVENTION

The present invention relates to cluster-type multifunctional magnetic-optical nanoparticles, which are composed of heterogeneous nanoparticles of magnetic nanoparticles and quantum dot nanoparticles and are capable of realizing both magnetic and optical functions at the same time, a method of preparing the same, and a method of detecting a specific material and cell imaging using the same.

More specifically, the present invention provides a platform for the preparation of multifunctional nanoparticles of various configurations, and relates to magnetic separation using magnetic properties of the multifunctional magnetic-optical nanoparticles and optical performance improvement using magnetic concentration, and a method of preparing a probe for detecting biomolecules.

2. DISCUSSION OF RELATED ART

Existing in vitro diagnostic biomolecules detection methods include enzyme-linked immunosorbent assay (ELISA), flow cytometry, and the like, and in this case, there are the disadvantages that the instrument used is an imported product, which is expensive, and a lot of time is required for analysis. In addition, organic phosphors used for analysis have a short lifetime and a high possibility of errors in testing in terms of poor stability.

In order to solve this problem, nanomaterials with high detection sensitivity have been recently used from various viewpoints. Although upconversion nanoparticles or quantum dots are used, since the upconversion nanoparticles or quantum dots do not have magnetic properties, it is impossible to specifically separate biomolecules or proteins to be captured. Therefore, there is a disadvantage in that the process is complicated to use beads having magnetic properties or to extract specific molecules and proteins to be captured.

Although multifunctional nanoparticles composed of metals and ceramics, which have been presented as an alternative, are expected to have very high applicability, it is difficult to simultaneously have uniform magnetic and optical properties within a single nanoparticle, and the applicability is limited in that the magnetic nanoparticles cause quenching of the fluorescent quantum dots.

RELATED ART DOCUMENT

Patent Document

1. ACS Appl. Mater. Interfaces vol 10, pp 41935-41946 (2018)

SUMMARY OF THE INVENTION

An object of the present invention is to provide cluster-type multifunctional magnetic-optical nanoparticles composed of quantum dots having a fluorescence signal and metal oxide nanoparticles having magnetic properties, and a method of preparing the same.

Another object of the present invention is to provide a cell image using the optical properties and magnetic concentration of multifunctional magnetic-optical nanoparticles, and a method of detecting biomolecules or biomaterials.

Means to Solve the Problem

The present invention provides a method of preparing multifunctional magnetic-optical nanoparticles, including:

preparing magnetic nanoparticle clusters by mixing an oily phase containing magnetic nanoparticles and an aqueous phase containing a cationic surfactant;

coating the magnetic nanoparticle clusters with a water-soluble polymer; and preparing multifunctional magnetic-optical nanoparticles by mixing a cluster solution containing magnetic nanoparticle clusters coated with the water-soluble polymer and a quantum dot solution containing quantum dot nanoparticles;

the solvent of the cluster solution has a higher polarity index than the solvent of the quantum dot solution.

In addition, the present invention provides multifunctional magnetic-optical nanoparticles prepared by the above-described preparing method.

Effects of the Invention

The multifunctional magnetic-optical nanoparticles according to the present invention are composed of quantum dot nanoparticles and magnetic nanoparticles, and can also be functionalized with biocompatible polymers to specifically allow the capture and detection of biomolecules or biomaterials, as well as quantitative analysis using colorimetric and fluorescence signals.

Therefore, the multifunctional magnetic-optical nanoparticles of the present invention can be utilized in various biomedical fields such as disease diagnosis, cell separation and imaging.

BRIEF DESCRIPTION OF THE DRAWINGS

FIG. TA is a schematic diagram of the process of preparing multifunctional magnetic-optical nanoparticles composed of quantum dot nanoparticles and iron oxide nanoparticles.

In addition, FIG. 1B is a transmission electron microscopy (TEM) photograph of the iron oxide cluster nanoparticles prepared in (4) of Example 1, FIG. 1C is a transmission electron microscopy (TEM) photograph of the multifunctional magnetic-optical nanoparticles prepared in (5) of Example 1, and FIG. 1D shows the microfluidic size according to time of the prepared multifunctional magnetic-optical nanoparticles as measured with dynamic light scattering (DLS).

FIG. 2A shows the transmission electron micrograph, size distribution, and fluorescence spectrum measured by photoluminescence (PL) of the CdSe—CdS core-shell quantum dot nanoparticles prepared in (C) of Example 1. In addition, FIG. 2B shows the X-ray diffraction analysis data of CdSe—CdS quantum dots.

FIG. 3A shows a transmission electron microscopy photograph and X-ray diffraction analysis data of the iron oxide cluster prepared in (4) of Example 1.

In addition, FIG. 3B shows transmission electron microscopy and energy dispersive spectroscopy (EDS) photographs of the CdSe—CdS/$Fe_3O_4$ multifunctional magnetic-optical nanoparticles prepared in (5) of Example 1.

FIG. 3C shows X-ray diffraction analysis data of iron oxide clusters and CdSe—CdS/$Fe_3O_4$ multifunctional magnetic-optical nanoparticles.

FIG. 3D shows magnetic property data of iron oxide clusters and multifunctional magnetic-optical nanoparticles as measured with a vibrating sample magnetometer (VSM).

FIG. 4A shows a high-resolution TEM (HRTEM) photograph of the surface of the multifunctional magnetic-optical nanoparticles prepared in (5) of Example 1.

In addition, FIG. 4B shows the X-ray photoelectron spectroscopy (XPS) data of the multifunctional magnetic-optical nanoparticles.

FIG. 5A is a schematic diagram showing the process of modifying the antibody to the multifunctional magnetic-optical nanoparticles, magnetically concentrating the antigen accordingly, and detecting the fluorescence.

Also, FIG. 5B shows data obtained by quantitatively detecting the fluorescence of Adenovirus, Rotavirus, Respiratory syncytial virus (RSV), Influenza A/B virus, and Norovirus using multifunctional magnetic-optical nanoparticles.

FIG. 5C shows the results of imaging brain tumor cells (U87MG cells) with a confocal microscope using multifunctional magnetic-optical nanoparticles. In this case, blue indicates DAPI-stained cell nuclei, and red indicates multifunctional magnetic-optical nanoparticles.

DETAILED DESCRIPTION OF EXEMPLARY EMBODIMENTS

Hereinafter, the present invention will be specifically described.

The present invention relates to a method of preparing multifunctional magnetic-optical nanoparticles, the method including: (A) preparing a magnetic nanoparticle cluster by mixing an oily phase containing magnetic nanoparticles and an aqueous phase containing a cationic surfactant (hereinafter, magnetic nanoparticle cluster preparation step);

(B) coating the magnetic nanoparticle cluster with a water-soluble polymer (hereinafter, magnetic nanoparticle cluster coating step); and (C) preparing multifunctional magnetic-optical nanoparticles by mixing a cluster solution containing magnetic nanoparticle clusters coated with the water-soluble polymer and a quantum dot solution containing quantum dot nanoparticles (hereinafter, multifunctional magnetic-optical nanoparticle preparation step).

In the present invention, after forming clusters of magnetic nanoparticles through an oil-in-water emulsion method, quantum dot nanoparticles are penetrated into the clusters and physically combined therewith to prepare cluster-type magnetic-optical composite nanoparticles. The multifunctional magnetic-optical nanoparticles prepared by the preparation method according to the present invention can enhance the fluorescence signal by using magnetic concentration. In addition, the biomaterials can be detected using a colorimetric assay at the same time as quantitative analysis using the improved fluorescence signal.

In the present invention, (A) the magnetic nanoparticle cluster preparation step is a step of preparing a magnetic nanoparticle cluster by mixing an oily phase containing magnetic nanoparticles and an aqueous phase containing a cationic surfactant.

In the present invention, magnetic nanoparticles may be composed of clusters of magnetic nanoparticles through an oil-in-water emulsion method.

In the present invention, the oily phase may include magnetic nanoparticles.

In one embodiment, the magnetic nanoparticles may be metal oxide nanoparticles, wherein the metal oxide may include at least one selected from the group consisting of FeO, $Fe_2O_3$, $Fe_3O_4$, $CoFe_2O_4$, $NiFe_2O_4$, $MnFe_2O_4$, $TiO_2$, $ZrO_2$, $CeO_2$, $Al_2O_3$ and MgO. In the present invention, magnetism can be imparted to the finally prepared multifunctional magnetic-optical nanoparticles using the metal oxide.

In one embodiment, the magnetic nanoparticles may be prepared by a general preparation method in the art, for example, may be synthesized using an iron ion precursor, a solvent and a stabilizing agent. The iron ion precursor may be iron pentacarbonyl, the solvent may be 1-octadecene (ODE), and the stabilizing agent may be oleylamine (OAm), oleic acid (OA) dibenzylamine, octadecylamine or a mixture thereof. Magnetic nanoparticles coated with a hydrophobic group may be prepared through the synthesis process, and each of the magnetic nanoparticles may have hydrophobicity.

In one embodiment, the average particle diameter of the magnetic nanoparticles may be 1 to 20 nm, or 3 to 17 nm.

In one embodiment, the oily phase solvent may be chloroform, hexane, octane, toluene, or a mixture thereof.

In the present invention, the aqueous phase may contain a cationic surfactant.

In one embodiment, the cationic surfactant may be at least one selected from the group consisting of dodecyltrimethylammonium bromide (DTAB), cetyltrimethylammonium bromide (CTAB) and tetradecyltrimethylammonium bromide (TTAB), and DTAB may be used in the embodiment of the present invention.

In one embodiment, the aqueous phase solvent may be water, alcohol, acetone, DMSO, acetic acid, or a mixture thereof.

In one embodiment, when the aqueous phase and the oily phase are mixed, magnetic nanoparticle clusters may be formed through an oil-in-water emulsion method. Specifically, the magnetic nanoparticle cluster may have a form in which the magnetic nanoparticle cluster is located inside the micelle on which the cationic surfactant layer is formed. That is, it may have a shape in which a cationic surfactant is coated on the surface of the cluster of magnetic nanoparticles. Each of the magnetic nanoparticles constituting the cluster may have hydrophobicity.

The average particle diameter of the magnetic nanoparticle cluster is not particularly limited, and may be, for example, 50 to 500 nm, or 50 to 200 nm. The magnetic nanoparticle cluster may be spherical. In the present invention, the term "spherical" may encompass not only a sphere mathematically defined as a three-dimensional shape composed of all points at the same distance from one point, but also those having a apparently round shape.

In the present invention, (B) the magnetic nanoparticle cluster coating step is a step of coating the magnetic nanoparticle cluster prepared in step (A) with a water-soluble polymer.

The step may be performed by mixing a solution containing magnetic nanoparticle clusters and a solution containing a water-soluble polymer.

In one embodiment, the water-soluble polymer may include at least one selected from the group consisting of polyvinylpyrrolidone and polyacrylic acid.

In one embodiment, the solvent of the solution containing the water-soluble polymer may be ethylene glycol (EG).

In step (B), the cationic surfactant has high solubility in solvents such as ethylene glycol and thus comes off the surface of the magnetic nanoparticle cluster, and the magnetic nanoparticle cluster is coated with a water-soluble polymer. That is, a water-soluble polymer coating layer may be formed. Accordingly, the surface of the magnetic nanoparticle cluster may have hydrophilicity, and the internal magnetic nanoparticles may have a relatively hydrophobic state.

In the present invention, step (C) is a multifunctional magnetic-optical nanoparticle preparation step, which is a step of preparing multifunctional magnetic-optical nanoparticles by mixing a cluster solution containing magnetic nanoparticle clusters coated with the water-soluble polymer and a quantum dot solution containing quantum dot nanoparticles.

In the above step, the multifunctional magnetic-optical nanoparticles can be prepared by penetrating the quantum dot nanoparticles inside the magnetic nanoparticle cluster and physically combining therewith.

In one embodiment, the cluster solution may include magnetic nanoparticle clusters coated with the water-soluble polymer of the above-described step (B).

The solvent of the cluster solution may be ethanol, methanol, acetone, dimethyl sulfoxide, or a mixture thereof.

In one embodiment, the quantum dot solution may include quantum dot nanoparticles.

The quantum dot nanoparticles may impart optical properties to the multifunctional nanoparticles of the present invention. The quantum dot nanoparticles may include at least one selected from the group consisting of cadmium selenide-cadmium sulfide (CdSe—CdS), cadmium selenide (CdSe), cadmium sulfide (CdS), zinc oxide (ZnO), zinc selenide (ZnSe), zinc sulfide (ZnS), manganese-doped zinc sulfide (Mn-doped ZnS), indium phosphide (InP), and cesium lead halide ($CsPbBr_3$, $CsPbI_3$) quantum dots.

These quantum dot nanoparticles may be prepared through a general preparation method in the art, and specifically, may be synthesized using a quantum dot ion precursor, a reducing agent, and a stabilizing agent in an organic solvent. In this case, the quantum dot ion may be zinc, sulfur, manganese, cadmium, selenium, indium, phosphorus, cesium, lead, bromine or iodine.

In one embodiment, the quantum dot nanoparticles may be cadmium selenide-cadmium sulfide (CdSe—CdS).

In one embodiment, the cadmium selenide-cadmium sulfide (CdSe—CdS) may be prepared by adding a cadmium ion precursor, a sulfur ion precursor and a stabilizer to a solution containing cadmium selenide quantum dots and reacting the same.

The cadmium selenide may be synthesized using a selenium ion precursor, a cadmium ion precursor, a reducing agent, and a stabilizing agent. At least one selected from the group consisting of selenium powder and selenium oxide may be used as a selenium ion precursor, and at least one selected from the group consisting of cadmium oleate (Cd-oleate), cadmium oxide (CdO) and cadmium chloride may be used as a cadmium ion precursor. In addition, octadecylphosphonic acid (ODPA), trioctylphosphine oxide (TOPO) and trioctylphosphine (TOP) may be used as reducing agents and stabilizing agents.

In addition, when preparing cadmium selenide-cadmium sulfide, as a cadmium ion precursor, at least one selected from the group consisting of cadmium oleate (Cd-oleate), cadmium oxide (CdO) and cadmium chloride may be used, and as the sulfur ion precursor, at least one selected from the group consisting of 1-octanethiol, sulfur powder and 1-dodecanethiol may be used. At least one selected from the group consisting of dibenzylamine, oleylamine (OAm), oleic acid (OA) and octadecylamine may be used as a reducing agent and stabilizing agent, and at least one selected from the group consisting of octadecene (ODE), dimethylformamide (DMF), and toluene may be used as a solvent.

In one embodiment, when using cadmium selenide-cadmium sulfide, it is possible to control the emission wavelength according to the thickness of the cadmium sulfide (CdS) shell, and properties may change depending on the total amount of the shell-forming precursor.

In addition, the amount of the shell-forming precursor in cadmium selenide-cadmium sulfide may be 300 nmol to 1500 nmol, and the proportion of cadmium sulfide (CdS) shell may be 15% to 60 wt % based on the entire particle.

In one embodiment, the size of the quantum dot nanoparticles may be 3 to 15 nm.

In one embodiment, the solvent of the quantum dot nanoparticle solution may be chloroform, isopropanol, or a mixture thereof.

The solvent of the cluster solution may have a higher polarity index than the solvent of the quantum dot solution. Specifically, the difference in polarity between the solvent of the cluster solution and the solvent of the quantum dot solution may be 0.5 to 2, or 1 to 2. That is, the quantum dot solution may have a property of being more hydrophobic than the cluster solution.

In one embodiment, the inside of the magnetic nanoparticle cluster coated with the water-soluble polymer has hydrophobicity compared to the outside. When quantum dot nanoparticles are injected into a cluster solution having hydrophilicity, the quantum dot nanoparticles have hydrophobic properties and thus penetrate into the magnetic nanoparticle clusters having the same hydrophobic properties. Accordingly, the magnetic nanoparticles having a relatively hydrophilic property compared to the quantum dot nanoparticles are pushed to the surface, and the quantum dot nanoparticles are located in the core, and multifunctional magnetic-optical nanoparticles having a structure in which magnetic nanoparticles are located in the shell can be prepared. Depending on the conditions of the reaction, the quantum dot nanoparticles may form a part of the shell of the multifunctional nanoparticles.

In one embodiment, the volume ratio of the magnetic nanoparticles and the quantum dot nanoparticles constituting the multifunctional magnetic-optical nanoparticles may be 3:0.1 to 3:1.

In one embodiment, the average particle diameter of the prepared multifunctional magnetic-optical nanoparticles may be 100 nm to 800 nm.

The present invention may further include the step of (D) coating the multifunctional magnetic-optical nanoparticles with a biocompatible polymer after performing the multifunctional magnetic-optical nanoparticle preparation step.

By coating the multifunctional magnetic-optical nanoparticles with a biocompatible polymer, the dispersibility of the multifunctional magnetic-optical nanoparticles can be improved. In addition, the attachment of the antibody can be easily performed in the application of the multifunctional magnetic-optical nanoparticles.

In one embodiment, the biocompatible polymer may include a functional group at the end of the biocompatible polymer. The biocompatible polymer itself may include a functional group, or a functional group may be introduced or modified at the end of the biocompatible polymer.

The functional group may include at least one selected from the group consisting of an amine group (—$NH_2$), a thiol group (—SH), a carboxyl group (—COOH) and a hydroxyl group (—OH).

In one embodiment, the biocompatible polymer may be at least one selected from the group consisting of polyacrylic acid (PAA), polyethylene glycol (PEG), polylactic acid (PLA) and polyglycolic acid (PGA). At this time, polyethylene glycol (PEG) may be modified with an amine group (—$NH_2$), a thiol group (—SH) and/or a hydroxyl group (—OH) at the end thereof.

In addition, the present invention relates to multifunctional magnetic-optical nanoparticles. The multifunctional magnetic-optical nanoparticles according to the present invention may be prepared by the above-described preparation method.

The multifunctional magnetic-optical nanoparticles may include a core including quantum dot nanoparticles; and a shell including magnetic nanoparticles and the quantum dot nanoparticles. The content of the quantum dot nanoparticles in the shell may be 40 wt % or less based on the total weight of the shell.

In one embodiment, the core may refer to a spherical portion composed of quantum dot nanoparticles in the multifunctional magnetic-optical nanoparticles. At this time, "spherical" may encompass not only a sphere mathematically defined as a three-dimensional shape composed of all points at the same distance from one point, but also those having a apparently round shape.

In one embodiment, the shell surrounds the sphere, and may be composed of only magnetic nanoparticles, or may be composed of the magnetic nanoparticles and quantum dot nanoparticles. The content of quantum dot nanoparticles in the shell may be 0 to 40 wt %, 1 to 30 wt %, or 1 to 20 wt % based on the total weight (100 wt %) of the shell.

In one embodiment, the surface of the multifunctional magnetic-optical nanoparticles may be coated with a biocompatible polymer. The biocompatible polymer may be the above-described biocompatible polymer, and a functional group may be formed at the end of the biocompatible polymer. Through this, the dispersibility of the multifunctional magnetic-optical nanoparticles can be improved, and the attachment of the antibody can be easily performed in the application of the multifunctional magnetic-optical nanoparticles.

The multifunctional magnetic-optical nanoparticles according to the present invention may simultaneously implement magnetic and optical functions by including magnetic nanoparticles and quantum dot nanoparticles.

Since the magnetic nanoparticles can act as a quencher to quench fluorescence, the closer the magnetic nanoparticles and the fluorescent material are, the greater the effect is. In the present invention, since the quantum dot nanoparticles are aggregated in the core portion of the multifunctional magnetic-optical nanoparticles, the proportion of the magnetic nanoparticles in the shell portion and the quantum dot nanoparticles that are not adjacent to each other is increased. In the present invention, interference with magnetic nanoparticles can be reduced through this, and strong fluorescence can be exhibited.

In addition, the present invention relates to a composition for imaging including the above-described multifunctional magnetic-optical nanoparticles, a kit for detecting an analyte, or a molecular diagnostic chip.

In addition, the present invention relates to a method of imaging or detecting an analyte, including: functionalizing the surface of the multifunctional magnetic-optical nanoparticles with a biomolecule capable of binding to an analyte to be detected;

exposing the functionalized multifunctional magnetic-optical nanoparticles to a sample containing one or more analytes; and identifying the analyte bound to the multifunctional magnetic-optical nanoparticles using photoluminescence spectroscopy.

The multifunctional magnetic-optical nanoparticles according to the present invention are functionalized with a biomolecule capable of recognizing an analyte to be detected, and thus can be used as a probe that can be applied to detect various target biomolecules.

In one embodiment, the analyte to be detected may include amino acids, peptides, polypeptides, proteins, glycoproteins, lipoproteins, nucleosides, nucleotides, oligonucleotides, nucleic acids, sugars, carbohydrates, oligosaccharides, polysaccharides, fatty acids, lipids, hormones, metabolites, cytokines, chemokines, receptors, neurotransmitters, antigens, allergens, antibodies, substrates, metabolites, cofactors, inhibitors, drugs, pharmaceuticals, nutrients, prions, toxins, explosives, pesticides, chemical weapons, biohazard agents, radioactive isotopes, vitamins, heterocyclic aromatic compounds, carcinogens, mutagens, anesthetics, amphetamines, barbiturates, hallucinogens, waste or contaminants. In addition, when the analyte is a nucleic acid, the nucleic acid may include genes, viral RNA and DNA, bacterial DNA, fungal DNA, mammalian DNA, cDNA, mRNA, RNA and DNA fragments, oligonucleotides, synthetic oligonucleotides, modified oligonucleotides, single-stranded and double-stranded nucleic acids, natural and synthetic nucleic acids.

In one embodiment, the biomolecule capable of recognizing an analyte and capable of binding to the surface of the multifunctional nanoparticles according to the present invention may include antibodies, antibody fragments, genetically engineered antibodies, single chain antibodies, receptor proteins, binding proteins, enzymes, inhibitor proteins, lectins, cell adhesion proteins, oligonucleotides, polynucleotides, nucleic acids or aptamers.

The photoluminescence spectroscopy method using the multifunctional magnetic-optical nanoparticles according to the present invention may exhibit a stronger signal intensity due to the structure of the multifunctional nanoparticles, so that detection may be possible even when the amount of the analyte is small. In addition, magnetic separation of analytes combined with multifunctional magnetic-optical nanoparticles is possible using magnetic properties, and can be used for very sensitive biomolecular analysis, and is very useful as in vitro diagnostic and imaging technology.

Hereinafter, the present invention will be described in more detail through specific examples. These examples are for illustrative purposes only, and it is obvious that the scope of the present invention is not limited to the presented examples.

EXAMPLES

Example 1. Preparation of Multifunctional Magnetic-Optical Nanoparticles (1) Synthesis of Magnetite ($Fe_3O_4$) Nanoparticles Iron oxide, specifically, magnetite ($Fe_3O_4$), nanoparticles were synthesized through a pyrolysis method.

In the reaction, iron pentacarbonyl ($Fe(CO)_5$) was used as an iron ion precursor, 1-octadecene (ODE) was used as a solvent, and oleic acid (OA) was used as a stabilizing agent.

After adding 1.5 mL of OA to 20 mL of ODE in a three-necked flask, it was rapidly heated to 100° C. for 5 minutes with magnetic stirring. When the solution temperature reached 100° C., 0.4 mL of $Fe(CO)_5$ was injected and then the temperature was maintained for 20 minutes. After heating to 180° C. for 10 minutes, the temperature was further maintained for 1 hour. As a final step, after removing the equipment for magnetic stirring, the solution was heated to 295° C. for 10 minutes in a nitrogen ($N_2$) atmosphere, and the reaction was carried out for 1 hour. After cooling, the resultant was washed with acetone and dispersed in 10 mL of chloroform (preparation of magnetite nanoparticle solution).

(2) Synthesis of Cadmium Selenide Quantum Dots

Cadmium selenide (CdSe) quantum dots were synthesized through a hot-injection synthesis method.

In the reaction, cadmium oxide (CdO) was used as a cadmium ion precursor, selenium powder as a selenium ion precursor, and octadecylphosphonic acid (ODPA), trioctylphosphine oxide (TOPO) and trioctylphosphine (TOP) were used as reducing agents and stabilizing agents, respectively.

120 mg of selenium powder and 1 mL of TOP were each magnetically stirred in a vial while increasing the temperature, and then mixed together until a transparent solution was obtained (preparation of Se-TOP precursor solution).

After putting 120 mg of CdO, 560 mg of ODPA and 6 g of TOPO in a three-necked flask, it was heated to 150° C. in a vacuum environment for 5 minutes and then maintained for 1 hour. Then, it was switched to a nitrogen atmosphere and heated to 380° C. for 10 minutes. When the solution reached 360° C., 4 mL of TOP was injected, and the Se-TOP precursor solution prepared in advance at 380° C. was injected. The reaction proceeded for 3 minutes and then rapid cooling was performed. Then, the resultant was washed with acetone, and dispersed in 10 mL of chloroform (preparation of cadmium selenide quantum dot solution).

(3) Cadmium Selenide-Cadmium Sulfide Quantum Dot Nanoparticles

Cadmium selenide-cadmium sulfide (CdSe—CdS) core-shell quantum dot nanoparticles were synthesized.

In the reaction, based on the CdSe quantum dots prepared in (2) above, oleylamine (OAm) and OA were used as stabilizing agents, cadmium oleate (Cd-oleate) and 1-octanethiol were used as ion precursors, and ODE was used as a solvent.

500 nmol of CdSe dispersed in chloroform, 10 mL of OAm, and 10 mL of ODE were placed in a three-necked flask, and a vacuum atmosphere was created at room temperature for 1 hour. Then, the solution was rapidly heated to 120° C. for 5 minutes in a vacuum environment and maintained for 20 minutes to evaporate the remaining moisture and chloroform. Then, the resultant was heated to 310° C. for 10 minutes while nitrogen was injected. When the aqueous solution temperature reached 240° C., the precursor injection was started. ODE was used to adjust the concentrations of 0.1 M Cd-oleate and 0.12 M 1-octanethiol, and 1.5 mL each was injected every 10 minutes. Then, 1 mL of OA was injected every hour to stabilize the shell-forming reaction. The thickness of the cadmium sulfide shell can be controlled by controlling the number of injections. After the last precursor solution was injected, 1 mL of OA was injected and the reaction was maintained at 310° C. for 1 hour. After cooling, the resultant was washed with hexane and acetone and dispersed in chloroform to a concentration of 50 μM (preparation of cadmium selenide-cadmium sulfide quantum dot nanoparticle solution).

(4) Iron Oxide Cluster Particles

The iron oxide particles were formed into clusters using a water-oil emulsion formation method.

In the reaction, chloroform, $H_2O$, ethylene glycol (EG) was used as a solvent, dodecyltrimethylammonium bromide (DTAB) was used as a surfactant, and polyvinylpyrrolidone (PVP, Mw: 29,000 Da) was used as a stabilizing agent. 2 mL of $H_2O$ to which 8 mg of DTAB was added and 2 mL of the $Fe_3O_4$ nanoparticle solution prepared in (1) above were placed in a flask, and then mixed using an ultrasonic disperser. Thereafter, shaking was performed at room temperature until all the chloroform was evaporated. The solution was put into 3 mL of EG adjusted to a concentration of 2 mM of PVP, and shaken at room temperature for 2 hours, and the surface was coated with PVP, a water-soluble polymer. Then, the resultant was washed with ethanol and dispersed in 5 mL of ethanol (preparation of iron oxide cluster particle solution).

(5) Cluster-Type Quantum Dot/Iron Oxide Multifunctional Magnetic-Optical Nanoparticles Cluster-type quantum dot/iron oxide (CdSe—CdS/$Fe_3O_4$) multifunctional magnetic-optical nanoparticles have a structure in which iron oxide cluster nanoparticles and CdSe—CdS quantum dot nanoparticles are combined.

In the reaction, $H_2O$, chloroform and ethanol were used as a solvent, polyvinylpyrrolidone (PVP, Mw: 29,000 Da) as a stabilizing agent, sodium poly(acrylic acid) (Na-PAA, Mw: 2,100 Da) as a stabilizing agent and a carboxyl group (—COOH)) as a precursor.

After putting 3 mL of the iron oxide cluster particle solution prepared in (4) into a vial, 1 mL of the cadmium selenide-cadmium sulfide quantum dot nanoparticle solution prepared in (3) was added, 4 mL of chloroform was additionally injected, and was shaken for 10 minutes. The CdSe—CdS quantum dots penetrated into the iron oxide cluster, and the overall size of the multifunctional magnetic-optical nanoparticles grew. After washing with ethanol, shaking was performed for 30 minutes in ethanol having a concentration of 0.4 mM of PVP for stabilization. Then, the resultant was washed with water and dispersed in 5 mL of water.

Then, 5 mL of Na-PAA at a concentration of 20 mg/mL was injected for dispersibility in aqueous solution and antibody attachment, and multifunctional magnetic-optical nanoparticle coating was performed for 20 minutes. Then, the resultant was washed with $H_2O$ and dispersed in 8 mL of $H_2O$.

Experimental Example 1. Physical Properties of Multifunctional Magnetic-Optical Nanoparticles FIG. 1A is a schematic diagram of the process of preparing multifunctional magnetic-optical nanoparticles composed of quantum dot nanoparticles and iron oxide nanoparticles.

In addition, FIG. 1B is a transmission electron microscopy (TEM) photograph of the iron oxide cluster nanoparticles prepared in (4) of Example 1, FIG. 1C is a transmission electron microscopy (TEM) photograph of the multifunctional magnetic-optical nanoparticles prepared in (5) of Example 1, and FIG. 1D shows the microfluidic size according to time of the prepared multifunctional magnetic-optical nanoparticles as measured with dynamic light scattering (DLS).

As shown in a to FIG. 1D, according to the present invention, multifunctional magnetic-optical nanoparticles having a size of 100 to 800 nm are synthesized, and it can be confirmed that the quantum dot particles are physically adsorbed to the magnetic cluster nanoparticles.

In addition, by coating the prepared multifunctional magnetic-optical nanoparticles with PAA, it can be confirmed that the multifunctional magnetic-optical nanoparticles have dispersibility in an aqueous solution and their structure is stable over time.

FIG. 2A shows the transmission electron micrograph, size distribution, and fluorescence spectrum measured by photoluminescence (PL) of the CdSe—CdS core-shell quantum dot nanoparticles prepared in (C) of Example 1. In addition, FIG. 2B shows the X-ray diffraction analysis data of CdSe—CdS quantum dots.

The light emission intensity can be measured using the photoluminescence spectrometer, and in this case, the excitation wavelength was set to 365 nm.

As shown in FIGS. 2*a* and 2*b*, it can be confirmed that two types of quantum dots exhibiting emission wavelengths at 620 nm and 570 nm were prepared by the present invention. In particular, in the present invention, it is possible to control the emission wavelength according to the thickness of the cadmium sulfide (CdS) shell, and properties may change depending on the total amount of the shell-forming precursor. In addition, based on X-ray diffraction analysis, it can be seen that the 20 positions of the selenium-cadmium and the cadmium sulfide are consistent with the X-ray diffraction data of the quantum dots synthesized in the present invention, confirming that cadmium sulfide-cedmium selenide quantum dots were prepared.

FIG. 3A shows a transmission electron microscopy photograph and X-ray diffraction analysis data of the iron oxide cluster prepared in (4) of Example 1.

FIG. 3B shows transmission electron microscopy and energy dispersive spectroscopy (EDS) photographs of the CdSe—CdS/$Fe_3O_4$ multifunctional magnetic-optical nanoparticles prepared in (5) of Example 1.

FIG. 3C shows X-ray diffraction analysis data of iron oxide clusters and CdSe—CdS/$Fe_3O_4$ multifunctional magnetic-optical nanoparticles.

In addition, FIG. 3D shows magnetic property data of iron oxide clusters and multifunctional magnetic-optical nanoparticles as measured with a vibrating sample magnetometer (VSM).

As shown in FIGS. 3*a*-3*d*, in the multifunctional magnetic-optical nanoparticles, it can be confirmed that the magnetic nanoparticles are located in the shell region, and the quantum dot nanoparticles are present in the inner region. In addition, the presence of iron oxide nanoparticles and quantum dot nanoparticles can be confirmed by the 20 position in the X-ray diffraction data, and the VSM can be used for measurement to confirm that the multifunctional magnetic-optical nanoparticles have a 16 emu/g saturation magnetization and a remanent magnetization and coercive force of 0.

In addition, FIG. 4A shows a high-resolution TEM (HR-TEM) photograph of the surface of the multifunctional magnetic-optical nanoparticles prepared in (5) of Example 1.

FIG. 4B shows the X-ray photoelectron spectroscopy (XPS) data of the multifunctional magnetic-optical nanoparticles.

As shown in a and FIG. 4B, as a result of analyzing the crystal plane by high-resolution TEM, it can be confirmed that the quantum dot nanoparticles and iron oxide nanoparticles are located on the surface of the multifunctional magnetic-optical nanoparticles. In addition, the presence of quantum dots and iron oxide nanoparticles on the surface can be confirmed based on the XPS data. Additionally, it can be confirmed that the PAA coating is formed on the surface by checking the binding energy of O 1s and C 1s.

Experimental Example 2. Viral Antigen Detection and Cell Imaging Using Multifunctional Magnetic-Optical Nanoparticles 0.1 mL of a 1-ethyl-3-(-3-dimethylaminopropyl) carbodiimide hydrochloride (EDC) (20 mM) solution and 0.1 mL of a sulfo-N-hydroxysulfosuccinimide (NHS) (20 mM) solution were added to 1 mL of multifunctional magnetic-optical nanoparticles functionalized with a carboxyl group prepared in Example 1 and mixed, and then the reaction was carried out by shaking for at least 30 minutes. Then, the resultant was washed with phosphate buffer saline (PBS) and dispersed in 1 mL of PBS.

Then, 0.1 mL of an antibody solution (0.1 mg/mL) of Adenovirus, Rotavirus, Respiratory syncytial virus (RSV), Influenza A/B virus, and Norovirus (0.1 mg/mL) was added to each nanoparticle solution, and stirring was performed for at least 1 hour. Then, the resultant was washed with PBS and dispersed in 1 mL of PBS.

1 mL of 1% bovine serum albumin (BSA) dissolved in PBS was added to the solution, and then the remaining reactor was blocked by shaking for an additional 60 minutes. After washing with PBS, the resultant was dispersed in 1 mL of BSA 0.2% dissolved in Tris-HCl buffer (0.01 M, pH 8.5).

The concentration of each solution of the multifunctional magnetic-optical nanoparticles surface-functionalized with the Adenovirus, Rotavirus, RSV, Influenza A/B virus and Norovirus antibody was lowered to 1/10, and a minimum of 2 μL of the multifunctional magnetic-optical nanoparticle solution was mixed with 50 μL of a corresponding viral antigen in a 96 well plate and then reacted with an antibody-functionalized nitrocellulose membrane for at least 10 minutes, and further, a rapid buffer was flowed for 10 minutes to minimize non-specific binding. Then, the resultant was detected by putting it in a fluorescence diagnostic device.

An antigen enrichment experiment using magnetism was carried out as follows. The concentration of the multifunctional nanoparticle solution surface-functionalized with the Adenovirus and Rotavirus antibodies was lowered to 1/10 and a minimum of 20 μL of the compound-functional cluster nanoparticle solution was added to a microtube with 500 μL of a corresponding viral antigen, and reacted by pipetting. Then, a permanent magnet was placed at the bottom of the microtube and magnetic concentration was performed for 10 minutes, then the supernatant was removed and re-dispersed in 50 μL of rapid buffer. After transferring this to a 96-well plate, it was reacted with an antibody-functionalized nitrocellulose membrane for at least 10 minutes, and non-specific binding was minimized using a rapid buffer for an additional 10 minutes. The resultant was detected by putting it in a fluorescence diagnostic device.

In addition, carboxyl-functionalized multifunctional magnetic-optical nanoparticles were incubated with U87MG cells for 1 hour and fixed. Cell nucleus staining was performed using 4'6-diamidino-2-phenylidole (DAPI), and measurement was made with a confocal laser scanning microscope (Confocal Microscopy).

FIG. 5A is a schematic diagram showing the process of modifying the multifunctional magnetic-optical nanoparticles with the antibody, magnetically concentrating the antigen accordingly, and detecting the fluorescence.

FIG. 5B shows data obtained by quantitatively detecting the fluorescence of Adenovirus, Rotavirus, Respiratory syncytial virus (RSV), Influenza A/B virus, and Norovirus using multifunctional magnetic-optical nanoparticles.

In addition, FIG. 5C shows the results of imaging brain tumor cells (U87MG cells) with a confocal microscope using multifunctional magnetic-optical nanoparticles. At this time, blue indicates DAPI-stained cell nuclei, and red indicates multifunctional magnetic-optical nanoparticles.

From FIG. 5B, it can be confirmed that fluorescence intensity varied depending on the infection concentration, and that the fluorescence intensity of a low concentration antigen increased during magnetic concentration as compared to a sample that did not undergo concentration. In addition, from FIG. 5C, it can be confirmed that the red multifunctional magnetic-optical nanoparticles were distributed around the cell nuclei stained blue, so that enable cell imaging is possible.

What is claimed is:

1. A method of preparing multifunctional magnetic-optical nanoparticles, including:

preparing magnetic nanoparticle clusters by mixing an oily phase containing magnetic nanoparticles and an aqueous phase containing a cationic surfactant;

coating the magnetic nanoparticle clusters with a water-soluble polymer; and preparing multifunctional magnetic-optical nanoparticles by mixing a cluster solution containing magnetic nanoparticle clusters coated with the water-soluble polymer and a quantum dot solution containing quantum dot nanoparticles, wherein the solvent of the cluster solution has a higher polarity index than the solvent of the quantum dot solution, and wherein the cationic surfactant includes one or more selected from the group consisting of dodecyltrimethylammonium bromide (DTAB), cetyltrimethylammonium bromide (CTAB) and tetradecyltrimethylammonium bromide (TTAB).

2. The method of claim 1, wherein the magnetic nanoparticles are metal oxide nanoparticles including one or more selected from the group consisting of FeO, $Fe_2O_3$, $Fe_3O_4$, $CoFe_2O_4$, $NiFe_2O_4$, $MnFe_2O_4$, $TiO_2$, $ZrO_2$, $CeO_2$, $Al_2O_3$ and MgO.

3. The method of claim 1, wherein the solvent of the oily phase is chloroform, hexane, octane, toluene, or a mixture thereof.

4. The method of claim 1, wherein the solvent of the aqueous phase is water, alcohol, acetone, dimethyl sulfoxide (DMSO), acetic acid, or a mixture thereof.

5. The method of claim 1, wherein the average particle diameter of the magnetic nanoparticle clusters is 50 to 500 nm.

6. The method of claim 1, wherein the water-soluble polymer includes one or more selected from the group consisting of polyvinylpyrrolidone and polyacrylic acid.

7. The method of claim 1, wherein the quantum dot nanoparticles include one or more selected from the group consisting of cadmium selenide-cadmium sulfide (CdSe—CdS), cadmium selenide (CdSe), cadmium sulfide (CdS), zinc oxide (ZnO), zinc selenide (ZnSe), zinc sulfide (ZnS), manganese-doped zinc sulfide (Mn-doped ZnS), indium phosphide (InP), and cesium lead halide ($CsPbBr_3$, $CsPbI_3$) quantum dots.

8. The method of claim 7, wherein the quantum dot nanoparticles are cadmium selenide-cadmium sulfide (CdSe—CdS), the cadmium selenide-cadmium sulfide is prepared by adding a cadmium ion precursor, a sulfur ion precursor and a stabilizing agent to a solution containing cadmium selenide quantum dots and reacting the same.

9. The method of claim 8, wherein the stabilizing agent is one or more selected from the group consisting of oleylamine (OAm), oleic acid (OA), dibenzylamine and octadecylamine.

10. The method of claim 1, wherein the solvent of the cluster solution is ethanol, methanol, acetone, dimethyl sulfoxide, or a mixture thereof, and the solvent of the quantum dot nanoparticle solution is chloroform, isopropanol, or a mixture thereof.

11. The method of claim 1, wherein the difference in polarity between a solvent of the cluster solution and a solvent of the quantum dot solution is 0.5 to 2.

12. The method of claim 1, wherein, in the step of preparing the multifunctional magnetic-optical nanoparticles, the quantum dot nanoparticles penetrate into the inside of the magnetic nanoparticle cluster to form multifunctional magnetic-optical nanoparticles.

13. The method of claim 1, wherein the size of the prepared multifunctional magnetic-optical nanoparticles is 100 to 800 nm.

14. The method of claim 1, further including coating the prepared multifunctional magnetic-optical nanoparticles with a biocompatible polymer.

15. The method of claim 14, wherein the biocompatible polymer include one or more functional groups selected from the group consisting of an amine group (—$NH_2$), a thiol group (—SH), a carboxyl group (—COOH) and a hydroxyl group (—OH) at an end of the biocompatible polymer.

16. The method of claim 14, wherein the biocompatible polymer includes one or more selected from the group consisting of polyacrylic acid (PAA), polyethylene glycol (PEG), polylactic acid (PLA) and polyglycolic acid (PGA).

17. A multifunctional magnetic-optical nanoparticle prepared by the preparing method of claim 1, the nanoparticle including:

a core including quantum dot nanoparticles; and a shell including magnetic nanoparticles and the quantum dot nanoparticles, the content of the quantum dot nanoparticles in the shell is 40% or less based on the total weight of the shell.

18. A composition for imaging including the multifunctional magnetic-optical nanoparticles of claim 17, a kit for detecting an analyte, or a molecular diagnostic chip.

19. A method of imaging or detecting an analyte, including:

functionalizing the surface of the multifunctional magnetic-optical nanoparticles of claim 17 with a biomolecule capable of binding to an analyte to be detected;

exposing the functionalized multifunctional magnetic-optical nanoparticles to a sample containing one or more analytes; and identifying the analyte bound to the multifunctional magnetic-optical nanoparticles using photoluminescence spectroscopy.

* * * * *